United States Patent
Chu et al.

(10) Patent No.: US 9,480,723 B2
(45) Date of Patent: Nov. 1, 2016

(54) **METHOD OF PREPARING AN EXTRACT OF *ANTRODIA CINNAMOMEA* HAVING AN ELEVATED ANTCIN C AND ZHANKUIC C CONTENT**

(71) Applicant: DSG TECHNOLOGY, INC., Taipei (TW)

(72) Inventors: Wen-Tin Chu, Taipei (TW); Yao-Ken Hung, Taipei (TW); Shorong-Shii Liou, Taipei (TW); I-Min Liu, Taipei (TW); Wei-Cheng Chen, Taipei (TW)

(73) Assignee: KINGLAND PROPERTY CORPORATION, LTD., Taipei (TW)

( * ) Notice: Subject to any disclaimer, the term of this patent is extended or adjusted under 35 U.S.C. 154(b) by 243 days.

(21) Appl. No.: 13/886,036

(22) Filed: May 2, 2013

(65) Prior Publication Data
US 2014/0328871 A1    Nov. 6, 2014

(51) Int. Cl.
| | |
|---|---|
| A61K 36/06 | (2006.01) |
| A61K 36/09 | (2006.01) |
| A61K 36/54 | (2006.01) |
| C12N 13/00 | (2006.01) |
| A61K 36/07 | (2006.01) |
| C12N 1/14 | (2006.01) |

(52) U.S. Cl.
CPC ............. *A61K 36/07* (2013.01); *C12N 1/14* (2013.01); *C12N 13/00* (2013.01)

(58) Field of Classification Search
CPC ... A61K 36/07; A61K 36/074; A61K 36/076
See application file for complete search history.

(56) References Cited

U.S. PATENT DOCUMENTS

| | | | |
|---|---|---|---|
| 8,122,636 B2 * | 2/2012 | Chen et al. | 47/1.1 |
| 8,309,611 B2 * | 11/2012 | Liu et al. | 514/690 |
| 2006/0089402 A1 * | 4/2006 | Hattori et al. | 514/424 |
| 2008/0102512 A1 * | 5/2008 | Tsai | 435/256.8 |
| 2008/0103195 A1 * | 5/2008 | Liu et al. | 514/464 |
| 2012/0178945 A1 | 7/2012 | Wu et al. | |

FOREIGN PATENT DOCUMENTS

TW    M414081 U1    10/2011

OTHER PUBLICATIONS

Website document entitled: "Terrarium Tek—Let's Grow Mushrooms". (available at http://www.mushroomsvideos.com/Terrarium-Tek). Archived to Jun. 20, 2008. Downloaded from website May 1, 2015.*
Yang et al. (2012) Bioprocess Biosyst. Eng. 35: 1251-1258.*
Lu et al. (2013) Pharmacology and Therapeutics 139: 124-156.*
Liu et al. (2012) Biochemical Engineering Journal 64: 48-54.*
Lin et al. (2011) J. Agric. Food Chem. 59: 7626-7635.*
Lin et al. (2006) Botanical Studies 47: 267-272.*
Lin et al. (2006) International Journal of Food Microbiology 108: 182-187.*
Jang et al. (2013) Mycobiology 41(1): 63-66.*
Hai-Wen Chu, A study on timber cultivation of Antrodia camphorata, Thesis for the Degree of Master, Jul. 25, 2005, Chaoyan University of Technology, Taiwan (with Abstract).
Jia-Yi Lin, Effect of light on triterpenoids and extracellular polysaccharides in Antrodia cinnamomea, Master Thesis, Jun. 2010, National Central Univ., Taiwan (with Abstract).

* cited by examiner

*Primary Examiner* — Chris R Tate
*Assistant Examiner* — Russell Fiebig
(74) *Attorney, Agent, or Firm* — Muncy, Geissler, Olds & Lowe, P.C.

(57) ABSTRACT

A method of culturing *Antrodia cinnamomea* and obtaining *Antrodia cinnamomea* with improved contents of antcin C and zhankuic acid C is disclosed in the invention. The method comprises: providing a wood segment of *Cinnamomum kanehirai*; inoculating a strain of *Antrodia cinnamomea* to the wood segment, to obtain the wood segment inoculated with the strain of *Antrodia cinnamomea* with 0.162 g dry weight of hyphae and mycelia of the strain of *Antrodia cinnamomea* per kg wood segment; and irradiating the wood segment inoculated with the strain of *Antrodia cinnamomea* by a light of wavelength of 600-700 nm to obtain a fruit body; wherein an irradiation time of the wood segment inoculated with the strain of *Antrodia cinnamomea* is 8-12 hours per day for 30-40 days.

6 Claims, 1 Drawing Sheet

METHOD OF PREPARING AN EXTRACT OF *ANTRODIA CINNAMOMEA* HAVING AN ELEVATED ANTCIN C AND ZHANKUIC C CONTENT

BACKGROUND OF THE INVENTION

1. Field of the Invention

The present invention generally relates to a method of culturing *Antrodia cinnamomea* and, more particularly, to a method of culturing *Antrodia cinnamomea* and obtaining a fruit body with improved contents of anctin C and zhankuic C. The present invention further relates to a method of manufacturing an alcoholic extract of *Antrodia cinnamomea* and obtaining the alcoholic extract of *Antrodia cinnamomea* with improved contents of antcin C and zhankuic C and a medication of suppressing viability of tumor cells.

2. Description of the Related Art

*Antrodia cinnamomea*, a precious traditional Chinese medicine in Taiwan, grows only on inner rotten walls of hollow materials from a conserving species of *Cinnamomum kanehirai*. Wild species *Antrodia cinnamomea* is rich in triterpenoids which are believed to possess effects such as anti-tumor, liver-protective, anti-dotal, anti-high blood lipid and pressure and immuno-modulating activities. As a result, wild species *Antrodia cinnamomea* becomes precious and expensive.

Due to several problems of wild species *Antrodia cinnamomea*, such as rare amount and difficulty in obtaining, industries tend to culture *Antrodia cinnamomea* by conventional methods, and produce mycelia and fruit bodies of *Antrodia cinnamomea*. Furthermore, physiologically active ingredients, such as triterpenoids, can be further extracted from the mycelia and fruit bodies of *Antrodia cinnamomea*.

Conventional methods for culturing *Antrodia cinnamomea* include: a conventional liquid fermentation method, a conventional solid culturing method and a conventional wood segment cultivation method. *Antrodia cinnamomea* cultured by the conventional liquid fermentation method has a rapid growth velocity. However, nutrients of the mycelia of *Antrodia cinnamomea* produced by the conventional liquid fermentation method are different from the wild species *Antrodia cinnamomea* due to different biochemical and physiological metabolism pathways. Although fruit bodies of *Antrodia cinnamomea* produced by the conventional solid culturing method produces fruit bodies similar with the wild species *Antrodia cinnamomea*, nutrients of fruit bodies of *Antrodia cinnamomea* still differ from the wild species *Antrodia cinnamomea*.

In the conventional wood segment cultivation method, *Antrodia cinnamomea* is inoculated to dying wood segments of *Cinnamomum kanehirai*. *Antrodia cinnamomea* grows on the *Cinnamomum kanehirai* and produces fruit bodies with nutrients the same as the wild species *Antrodia cinnamomea*. However, the conventional wood segment cultivation method has a culturing period of approximately 2-3 years, and a culturing environment during the culturing period should be kept at a proper temperature. Therefore, the conventional wood segment cultivation method has problems in high cost and long culturing period, and is not suitable for mass production.

SUMMARY OF THE INVENTION

It is therefore the objective of this invention to provide a method of culturing *Antrodia cinnamomea* producing *Antrodia cinnamomea* with improved contents of antcin C and zhankuic acid C, thereby improving nutrient value of *Antrodia cinnamomea*.

It is another objective of this invention to provide a method of culturing *Antrodia cinnamomea* being time- and cost-saved, thereby being beneficial for mass production of *Antrodia cinnamomea*.

It is yet another objective of this invention to provide a method of manufacturing an alcoholic extract of *Antrodia cinnamomea*, thereby providing the alcoholic extract of *Antrodia cinnamomea* with improved contents of antcin C and zhankuic acid C, which poses ability of suppressing viability of tumor cells.

It is yet another objective of this invention to provide a medication of suppressing viability of tumor cells, which the alcoholic extract of *Antrodia cinnamomea* is served as an active ingredient.

A method of culturing *Antrodia cinnamomea* comprises: providing a wood segment of *Cinnamomum kanehirai*; inoculating a strain of *Antrodia cinnamomea* to the wood segment, to obtain the wood segment inoculated with the strain of *Antrodia cinnamomea* with 0.162 g dry weight of hyphae and mycelia of the strain of *Antrodia cinnamomea* per kg wood segment; and irradiating the wood segment inoculated with the strain of *Antrodia cinnamomea* by a light of wavelength of 600-700 nm to obtain a fruit body; wherein an irradiation time of the wood segment inoculated with the strain of *Antrodia cinnamomea* is 8-12 hours per day for 30-40 days.

In a preferred form shown, the strain of *Antrodia cinnamomea* is pre-incubated in a liquid culture medium and the strain of *Antrodia cinnamomea* contains 8.1 g dry weight of hyphae and mycelia per liter liquid culture medium.

In a preferred form shown, the light has a wavelength of 660 nm.

In a preferred form shown, the light is a light-emitting diode (LED).

In a preferred form shown, the irradiation time of the wood segment inoculated with the strain of *Antrodia cinnamomea* is 8 hours per day.

In a preferred form shown, the irradiation time of the wood segment inoculated with the strain of *Antrodia cinnamomea* is for 30 days.

A method of manufacturing an alcoholic extract of *Antrodia cinnamomea* comprises: providing the fruit body mentioned above and obtaining an alcoholic extract of *Antrodia cinnamomea* by ultrasonic vibrating with 95% ethanol under 25° C.

A medication of suppressing viability of hepatic tumor cells comprises the alcoholic extract of *Antrodia cinnamomea*.

A medication of suppressing viability of lung tumor cells comprises the alcoholic extract of *Antrodia cinnamomea*.

A medication of suppressing viability of colorectal tumor cells comprises the alcoholic extract of *Antrodia cinnamomea*.

A medication of suppressing viability of sarcoma cells comprises the alcoholic extract of *Antrodia cinnamomea*.

A medication of suppressing viability of breast tumor cells comprises the alcoholic extract of *Antrodia cinnamomea*.

Further scope of the applicability of the present invention will become apparent from the detailed description given hereinafter. However, it should be understood that the detailed description and specific examples, while indicating preferable embodiments of the invention, are given by way of illustration only, since various others will become apparent from this detailed description to those skilled in the art.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

DETAILED DESCRIPTION OF THE INVENTION

Figure 1:
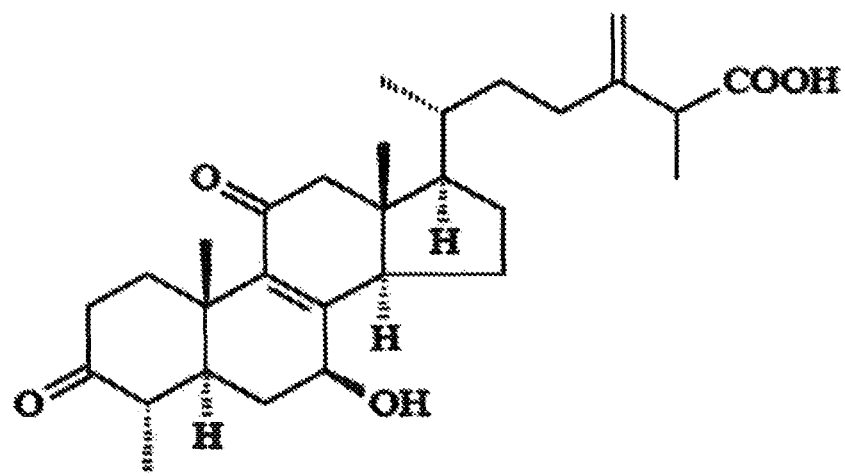
FIG. 1 is structural formula of antcin C.
Figure 2:
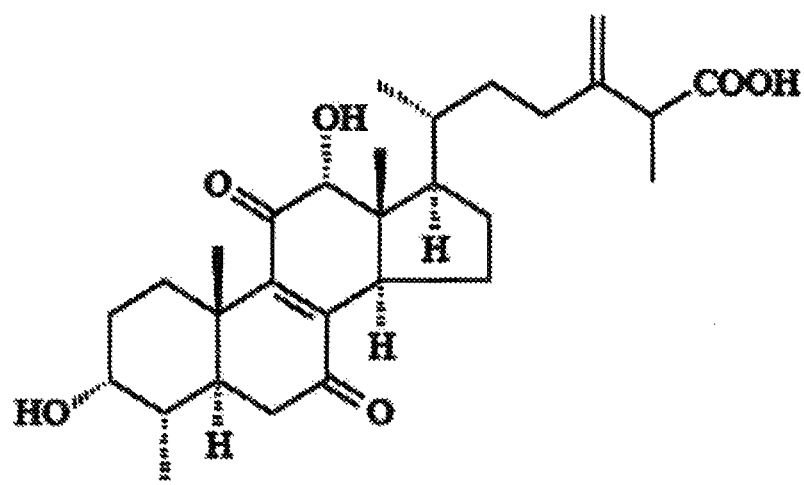
FIG. 2 is structural formula of zhankuic acid C.

An embodiment of a method of culturing *Antrodia cinnamomea* and producing a fruit body of *Antrodia cinnamomea* with improved contents of antcin C and zhankuic acid C according to preferred teachings of the present invention comprises: providing a wood segment of *Cinnamomum kanehirai*; inoculating a strain of *Antrodia cinnamomea* to the wood segment, to obtain the wood segment inoculated with the strain of *Antrodia cinnamomea* with 0.162 g dry weight of hyphae and mycelia of the strain of *Antrodia cinnamomea* per kg wood segment; and irradiating the wood segment inoculated with the strain of *Antrodia cinnamomea* by a light of wavelength of 600-700 nm to obtain a fruit body.

The wood segment of *Cinnamomum kanehirai* is maintained in a water-jacketed incubator with temperature of 28-30° C. and moisture of over 80%. Preferably, to avoid competition with other microorganisms, the wood segment of *Cinnamomum kanehirai* and the water-jacketed incubator are autoclaved before following steps.

The strain of *Antrodia cinnamomea* is inoculated to the wood segment of *Cinnamomum kanehirai*. For instance, the strain of *Antrodia cinnamomea* is, but not limited to, BRBC 35396 (purchased from the Food Industry Research and Development Institute in Taiwan). In this embodiment, the strain of *Antrodia cinnamomea* is pre-incubated in a liquid culture medium, and 1 liter of the strain of *Antrodia cinnamomea* containing 8.1 g dry weight of hyphae and mycelia per liter liquid culture medium is inoculated to 50 kg of the wood segment of *Cinnamomum kanehirai*. The strain of *Antrodia cinnamomea* can obtain sufficient growth space and nutrients from the wood segment of *Cinnamomum kanehirai*. Furthermore, in this embodiment, the strain of *Antrodia cinnamomea* is equally sprayed on surface of the wood segment of *Cinnamomum kanehirai*.

The wood segment inoculated with the strain of *Antrodia cinnamomea* is irradiated by a light of wavelength of 600-700 nm, and more particularly, the light is red light with wavelength of 660 nm. The light is preferably a light-emitting diode (LED) with benefits of high efficiency of photoelectric conversion, fixing wavelength, low production of heat. Furthermore, the light-emitting diode (LED) has benefit of easily adjusting an amount of light emission and a ratio of red light to blue light, thereby suitable to be used in a closed environment, such as the water-jacketed incubator. In this embodiment, the wood segment inoculated with the strain of *Antrodia cinnamomea* is irradiated with the light of wavelength of 660 nm for 8-12 hrs per day for 30-40 days. During the irradiating period, the strain of *Antrodia cinnamomea* inoculated to the wood segment grows to form a fruit body with improved contents of antcin C and zhankuic C. According to the embodiment, the fruit body with improved contents of antcin C and zhankuic C are obtained.

Furthermore, an embodiment of a method of manufacturing an alcoholic extract of *Antrodia cinnamomea* with improved contents of antcin C and zhankuic acid C according to preferred teachings of the present invention comprises: providing the fruit body as mentioned before and obtaining an alcoholic extract of *Antrodia cinnamomea* by ultrasonic vibrating with 95% ethanol under 25° C.

In detail, in this embodiment, 5 g of the fruit body of *Antrodia cinnamomea* is extracted by 600 ml, 95% ethanol under 25° C. using ultrasonic vibrating with frequency of 400 KHz, thereby active ingredients of *Antrodia cinnamomea*, such as triterpenoids, releasing to ethanol. Preferably, the fruit body of *Antrodia cinnamomea* is extracted thrice for 8 hours to obtain the alcoholic extract of *Antrodia cinnamomea* with improved contents of extracted active ingredients. A concentrated alcoholic extract of *Antrodia cinnamomea* is further obtained by frozen-drying.

In order to prove the method of culturing *Antrodia cinnamomea* of the invention can improve the contents of antcin C and zhankuic C of *Antrodia cinnamomea*, thereby providing a better efficiency on suppressing viability of tumor cell, contents of triterpenoids of the alcoholic extract of the invention are measured, and the alcoholic extract of the invention is used to suppress viability of tumor cell in vitro and in vivo.

(A) Measurement of Contents of Triterpenoids

The alcoholic extracts of *Antrodia cinnamomea* shown in Table 1 are used in this experiment. Group A1 is the alcoholic extract of this embodiment. Group A2 is an alcoholic extract which is not irradiated by the light of wavelength of 600-700 nm during culturing. 0.2 g of the two alcoholic extracts are ultrasonic vibrated with 5 ml of methanol for 15 min. followed by centrifugation at 3000 rpm for 10 min. 5 ml of supernatants are collected into new tubes, followed by heating with 100° C. water bath to dry.

TABLE 1

The alcoholic extracts of *Antrodia cinnamomea* used in this experiment

| Groups | Irradiation | Result |
|---|---|---|
| A1 | + | Table 2 |
| A2 | − | Table 3 |

Purospher STAR (purchased from Merck) RP-18e (5 μm) 250 mm×4 mm column is used. A mobile phase is acetonitrile and 0.085% phosphoric acid mixed in a volumetric ratio of 47:53. A flow rate of the mobile phase is 1 ml/min. Absorbance of 254 nm is detected for following analyses.

TABLE 2

Contents of triterpenoids of Group A1

| | Retention Time (min) | Peak Area | Percentage of Peak Area (%) |
|---|---|---|---|
| Antcin K | 8.880 | 719825 | 7.422 |
| | 9.360 | 1004373 | 10.355 |
| Antcin C | 31.187 | 1217384 | 12.552 |
| | 33.360 | 951016 | 9.802 |
| Zhankuic acid C | 35.087 | 1140242 | 11.756 |
| | 36.453 | 1686807 | 17.391 |
| Dehydrosulphurenic acid | 53.167 | 36474 | 0.376 |

TABLE 2-continued

Contents of triterpenoids of Group A1

| | Retention Time (min) | Peak Area | Percentage of Peak Area (%) |
|---|---|---|---|
| Zhankuic acid A | 61.460 | 591708 | 6.101 |
| | 62.140 | 380059 | 3.919 |
| Dehydroeburicoic acid | 95.347 | 51811 | 0.534 |

TABLE 3

Contents of triterpenoids of Group A2

| | Retention Time (min) | Peak Area | Percentage of Peak Area (%) |
|---|---|---|---|
| Antcin K | 8.893 | 1096424 | 13.949 |
| | 9.380 | 1352657 | 17.209 |
| Antcin C | 31.180 | 721911 | 9.185 |
| | 33.353 | 530136 | 6.745 |
| Zhankuic acid C | 35.093 | 567257 | 7.217 |
| | 36.460 | 871994 | 11.094 |
| Dehydrosulphurenic acid | 53.167 | 275409 | 3.504 |
| Zhankuic acid A | 61.420 | 356408 | 4.534 |
| | 62.093 | 217869 | 2.772 |
| Dehydroeburicoic acid | 95.307 | 95245 | 1.212 |

Tables 2 and 3 show contents of several triterpenoids, such as antcin K, antcin C, zhankuic C, dehydrosulphurenic acid, zhankuic acid A and dehydroeburicoic acid. Compared to group A2, group A1 shows improved contents of antcin C and zhankuic acid C. In other words, the method of culturing *Antrodia cinnamomea* of the invention can obtain the fruit body with improved contents of antcin C and zhankuic acid C.

(B) Effect on Viability of Tumor Cell In Vitro

As shown in Table 4, HepG2 (hepatic tumor cell line, in group B1-1 and B1-2), A549 (lung tumor cell line, in group B2-1 and B2-2), HCT-116 (colorectal tumor cell line, in group B3-1 and B3-2), S-180 (sarcoma cell line, in group B4-1 and B4-2), and MDA-MB-231 (breast tumor cell line, in group B5-1 and B5-2) are used in this experiment. All tumor cell lines are purchased from the Food Industry Research and Development Institute in Taiwan, and cultured in medium (Dulbecco's Modified Eagle Medium) containing 10% FBS (purchased from Biological Industries, Kibbutz beit haemek), 2 mmol/L $_L$-glutamine (purchased from HyClone, USA), 1× nonessential amino acids (purchased from HyClone, USA), 100 µg/ml streptomycin and 100 U/ml penicillin. All tumor cell lines are incubated in an incubator with temperature of 37° C., $CO_2$ concentration of 5% and humidity of 95%. Medium used for culturing the tumor cell lines are renewed once in two days.

TABLE 4

The tumor cell lines used in this experiment and viability thereof

| Groups | Cell Lines | The Alcoholic Extracts | Viability (%)* |
|---|---|---|---|
| B1-0 | Hepatic tumor cell | − | 100 |
| B1-1 | Hepatic tumor cell | + (with irradiated) | 36.21 ± 1.87 |
| B1-2 | Hepatic tumor cell | + (without irradiated) | 52.46 ± 1.36 |
| B2-0 | Lung tumor cell | − | 100 |
| B2-1 | Lung tumor cell | + (with irradiated) | 9.75 ± 1.06 |
| B2-2 | Lung tumor cell | + (without irradiated) | 37.64 ± 2.13 |
| B3-0 | Colorectal tumor cell | − | 100 |
| B3-1 | Colorectal tumor cell | + (with irradiated) | 12.85 ± 1.92 |
| B3-2 | Colorectal tumor cell | + (without irradiated) | 30.95 ± 2.37 |
| B4-0 | Sarcoma cell | − | 100 |
| B4-1 | Sarcoma cell | + (with irradiated) | 17.48 ± 2.04 |
| B4-2 | Sarcoma cell | + (without irradiated) | 28.52 ± 2.26 |
| B5-0 | Breast tumor cell | − | 100 |
| B5-1 | Breast tumor cell | + (with irradiated) | 29.05 ± 1.73 |
| B5-2 | Breast tumor cell | + (without irradiated) | 42.34 ± 2.63 |

*Cell Viability Rate (%) = (Absorbance of each testing set/Absorbance of a control set) × 100%

While subculturing, the tumor cell lines are centrifuged at 1000 rpm for 5 min to remove supernatants, followed by mixing with fresh medium. The tumor cell lines preferably have a concentration of $1\times10^5$-$1\times10^6$ cells/ml in 10 cm culturing dishes.

The culturing dishes 80-90% of bottom areas covered by the tumor cells are used in this experiment. Discolored medium is removed, 8 ml of PBS solution is used to wash the tumor cells and Trypsin/EDTA is added into the culturing dishes for 1-3 min. After the tumor cells dissociate with walls of the culturing dishes by slightly vortexing, the tumor cells are resuspended with prewarmed medium. The tumor cells are collected into centrifuge tubes, followed by centrifugation at 1500 rpm for 10 min. Supernatants are removed and the tumor cells are resuspended in medium containing FBS. 20 µl of the tumor cells are collected, and 20 µl of trypan blue is added to the tumor cells for staining. The stained tumor cells are collected in cell counters, and numbers of the stained tumor cells are counted under microscope. Only the tumor cells with viability over 85% are suitable for the following experiments.

Concentrations of the tumor cell lines are adjusted to $1\times10^5$ cells/ml by medium containing FBS. 100 µl of the tumor cell lines with a concentration of $1\times10^4$ cells/well are inoculated in a 96-well plate. The tumor cells lines are overnight cultured in an incubator with temperature of 37° C. and $CO_2$ concentration of 5%.

After culturing for 24 hrs, the alcoholic extracts of *Antrodia cinnamomea* with concentrations of 125 µg/ml (as shown in Table 4) are added into each well of the 96-well plate. The tumor cells lines are overnight cultured in an incubator with temperature being 37° C. and $CO_2$ concentration being 5%.

After culturing for 24 hours, medium is removed, and the tumor cells are washed by PBS solution. 100 µl of CCK-8 containing-fresh medium is added into each well of the 96-well plate. The tumor cells react with CCK-8 for 2 hours in the incubator (37° C., 5% $CO_2$), followed by vortexing for 5 min. Absorbance of 450 nm of the tumor cells in each well is detected.

As shown in Table 4, the alcoholic extracts of *Antrodia cinnamomea* can decrease viability of several types of tumor cells, such as the hepatic tumor (group B1-1 and B1-2), the lung tumor (group B2-1 and B2-2), the colorectal tumor (group B3-1 and B3-2), the sarcoma (group B4-1 and B4-2) and the breast tumor (group B5-1 and B5-2.) Furthermore, compared with group B1-2 (without irradiated), group B1-1 without irradiated has a better efficiency on reduction of viability of the tumor cells. Similar results can be observed in the lung tumor (group B2-1 and B2-2), the colorectal tumor (group B3-1 and B3-2), the sarcoma (group B4-1 and B4-2) and the breast tumor (group B5-1 and B5-2.)

(C) Effect on Viability of Tumor Cells In Vivo

Specific-pathogen free Balb/C male mice (8 week-old, weight 20-25 g) purchased from the animal center of the national Cheng Kung University are used in this experiment. The mice are housed in an animal room with constant temperature of 25±1° C. where is kept on a 12-hours light and 12-hours dark cycle. The mice are housed and kept on free diet and water, which provided by the animal center of the national Cheng Kung University.

The sarcoma cells, such as the S-180 cell lines purchased from the Food Industry Research and Development Institute in Taiwan are diluted to a concentration of $5 \times 10^6$ cells/ml by a saline solution. The diluted sarcoma cells are administered to underarm regions of the mice via subcutaneous injection.

The alcoholic extracts of *Antrodia cinnamomea* shown in Table 5 are administered via gastric gavage twice a day for 30 days. Tumor sizes are measured by X-ray imaging.

TABLE 5

The mice used in this experiment and the tumor sizes thereof

| Groups | The Alcoholic Extracts | Tumor Sizes (mm$^3$) |
|---|---|---|
| C0 | − | 1533.6 ± 27.8 |
| C1 | + (with irradiated) | 714.8 ± 20.6 |
| C2 | + (without irradiated) | 1056.7 ± 33.1 |

As shown in Table 5, compared with the mice in group C0, the mice administered with the alcoholic extract with irradiated (group C0 has a tumor size of 714.8±20.6 mm$^3$ decreasing by 53.4±6.7%. The mice administered with the alcoholic extract without irradiated (group C2) has a tumor size of 1056.7±33.1 mm$^3$ which reducing by 31.6±8.7%. As a result, the alcoholic extract of the invention has a better efficiency on inhibiting viability of tumor growth in vivo.

The alcoholic extract of *Antrodia cinnamomea* of the invention can effectively suppress viability of tumor cells, thereby being potential to be applied to pharmaceutical industry, being an active substance of medication or health products with anti-tumor activities. In the present invention, the alcoholic extract of *Antrodia cinnamomea* can be given to any target individually or combined with any acceptable excipients, for example carriers or other ingredients, and is capable of being further manufactured into any form of medicament, such as pill, capsule, powder, solution and pastil for easy and convenient delivery to targets.

In summary, according to the method of culturing *Antrodia cinnamomea* of the invention, the cultured *Antrodia cinnamomea* has improved contents of antcin C and zhankuic C, thereby improving nutrient value of *Antrodia cinnamomea*.

Furthermore, according to the method of culturing *Antrodia cinnamomea* of the invention, culturing period is effectively shortened, thereby improving economic value of *Antrodia cinnamomea*.

Moreover, according to the method of manufacturing an alcoholic extract of *Antrodia cinnamomea* of the invention, the alcoholic extract with improved amounts of antcin C and zhankuic C can effectively decrease viability of tumor cells. Therefore, the alcoholic extract is suitable to be used as an active ingredient to suppress viability of tumor cells.

Finally, the alcoholic extract of *Antrodia cinnamomea* of the invention is capable to serve as an active ingredient effectively suppressing viability of hepatic tumor cells, lung tumor cells, colorectal tumor cells, sarcoma cells and breast tumor cells. Therefore, induced cytotoxicity and apoptosis in tumor cells can prevent tumor from proliferation and metastasis.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A method of preparing an extract of *Antrodia cinnamomea* having an elevated antcin C and zhankuic C content comprising the steps of:
   (a) providing a wood segment of *Cinnamomum kanehirai*,
   (b) inoculating 0.162 g of dry weight of hyphae and mycelia of a strain of *Antrodia cinnamomea* per kilogram of the wood segment to produce an inoculated wood segment,
   (c) culturing the inoculated wood segment for 30-40 days under irradiation by light of wavelength 600-700 nm for 8-12 hours per day to obtain an *Antrodia cinnamomea* fruit body,
   (d) extracting the fruit body under ultrasonic conditions with 95% ethanol at a temperature under 25° C. to produce said extract having an elevated antcin C and zhankuic C content.

2. The method of claim 1, wherein before inoculating the strain of *Antrodia cinnamomea* to the wood segment, the strain of *Antrodia cinnamomea* is pre-incubated in a liquid culture medium and the strain of *Antrodia cinnamomea* contains 8.1 g dry weight of hyphae and mycelia per liter liquid culture medium.

3. The method of claim 1, wherein the light has a wavelength of 660 nm.

4. The method of claim 1, wherein the light is generated by a light-emitting diode (LED).

5. The method of claim 1, wherein the irradiation time of the wood segment inoculated with the strain of *Antrodia cinnamomea* is 8 hours per day.

6. The method of claim 1, wherein the irradiation time of the wood segment inoculated with the strain of *Antrodia cinnamomea* is for 30 days.

* * * * *